US00PP15692P2

(12) United States Plant Patent
Diboll

(10) Patent No.: US PP15,692 P2
(45) Date of Patent: Mar. 22, 2005

(54) ***SILENE* PLANT NAMED 'PRAIRIE FIRE'**

(50) Latin Name: *Silene regia*
Varietal Denomination: Prairie Fire

(76) Inventor: Neil Hart Diboll, P.O. Box 306, Westfield, WI (US) 53964-0306

( * ) Notice: Subject to any disclaimer, the term of this patent is extended or adjusted under 35 U.S.C. 154(b) by 44 days.

(21) Appl. No.: 10/795,778

(22) Filed: Mar. 8, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Penny J. Aguirre

(57) ABSTRACT

A new cultivar of Royal catchfly, *Silene regia* 'Prairie Sunset', characterized by its large, deep red flowers, its thick stems, its wide, ovate-shaped dark green leaves, and its usefulness as a cut flower.

2 Drawing Sheets

Botanical classification: *Silene regia.*
Varietal denomination: 'Prairie Fire'.

BACKGROUND OF THE INVENTION

The present invention relates to a new and distinct cultivar of *Silene regia* and will be referred to hereafter by its cultivar name, 'Prairie Fire'. 'Prairie Fire' represents a new Royal catchfly, an herbaceous perennial grown for landscape use.

The inventor discovered the new cultivar, 'Prairie Fire', in a cultivated field in Westfield, Wis. in the summer of 2000. 'Prairie Fire' was discovered as a naturally occurring mutant seedling in a cultivated production field that the inventor had sowed for seed production. The field was sown with seeds derived from unnamed plants of *Silene regia.*

The combined characteristics of 'Prairie Fire': its large, deep red flowers, its thick stems, and wide dark green leaves make this new cultivar unique and unlike any other known cultivars of *Silene regia* known to the inventor. The combined characteristics exhibited by 'Prairie Fire' indicate that the new cultivar is most likely a tetraploid, however, this theory has not been scientifically tested.

Asexual reproduction of the new cultivar was first accomplished by in vitro propagation in Waseca, Minn. in spring of 2001 under the direction of the inventor. The characteristics of the new cultivar have been determined to be stable and are reproduced true to type in successive generations.

SUMMARY OF THE INVENTION

The following traits have been repeatedly observed and represent the characteristics of the new cultivar as observed on plants grown for two years outdoors in Westfield, Wis. These attributes in combination distinguish 'Prairie Fire' from other varieties known to the inventor.

1. Large, red flowers that appear for about 5 to 6 weeks from mid July to late August. Flowers are typically about 4 cm in diameter, while a typical flower of *Silene regia* is about 2.5 cm in diameter.

2. The dark green leaves of the new cultivar are wider and more ovate in shape than those observed on plants of *Silene regia* of the same age. The leaves of *Silene regia* are more lanceolate in shape.

3. Flowers are borne on thick flower stalks, up to about 8 mm in diameter.

4. Useful for cut flower arrangements; the flowers remain attractive for 7 to 10 days in water.

5. Tolerant to a wide range of growing conditions, growing well in full sun to light shade and in well drained to moist soils.

BRIEF DESCRIPTION OF THE DRAWING

The plants and plant parts in the Figures depict a two-year old plant of 'Prairie Fire' in an outdoor trail bed in Westfield, Wis.

The photograph in FIG. 1 provides an overall view of the new *Silene* in bloom.

Figure 1:
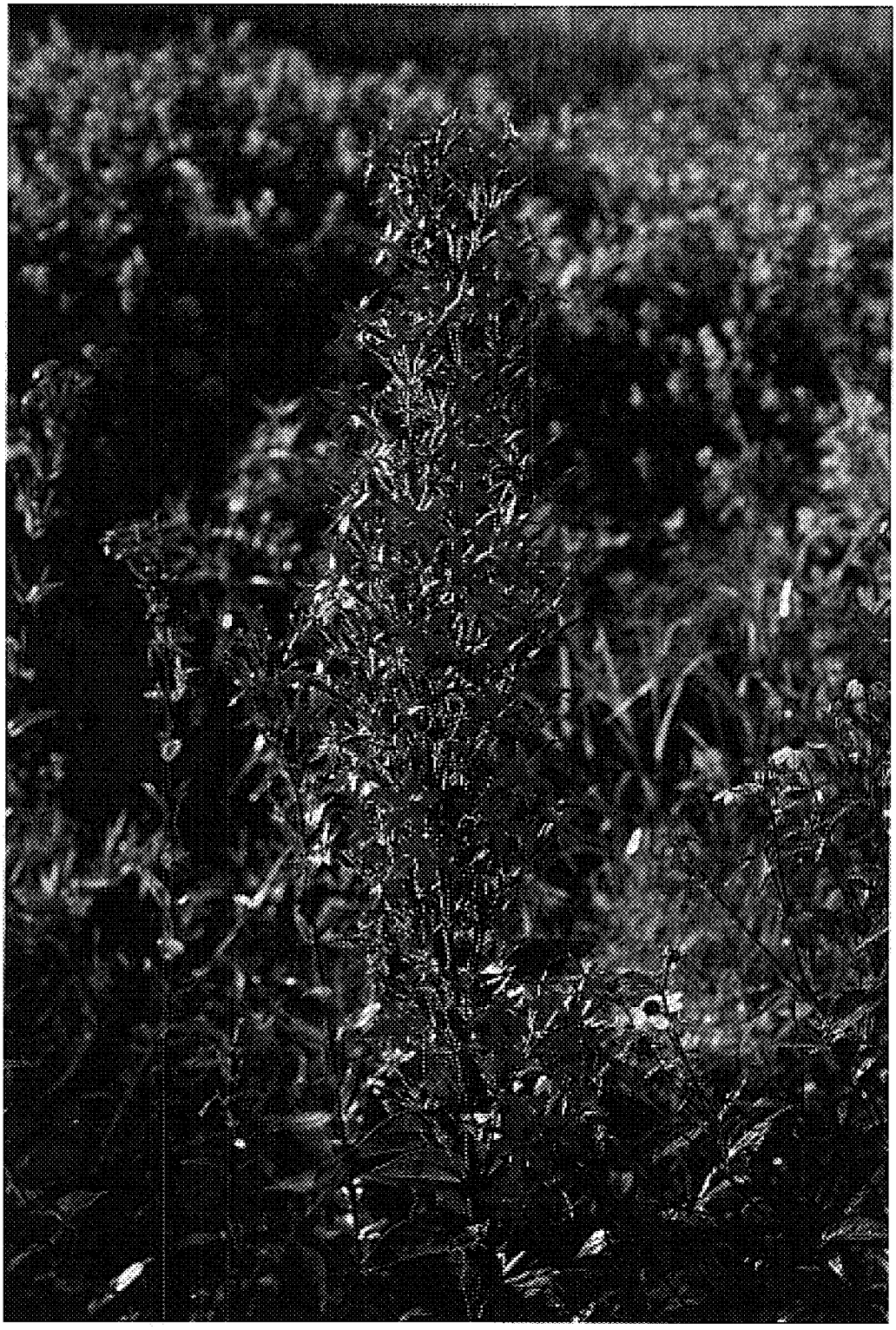
Figure 2:
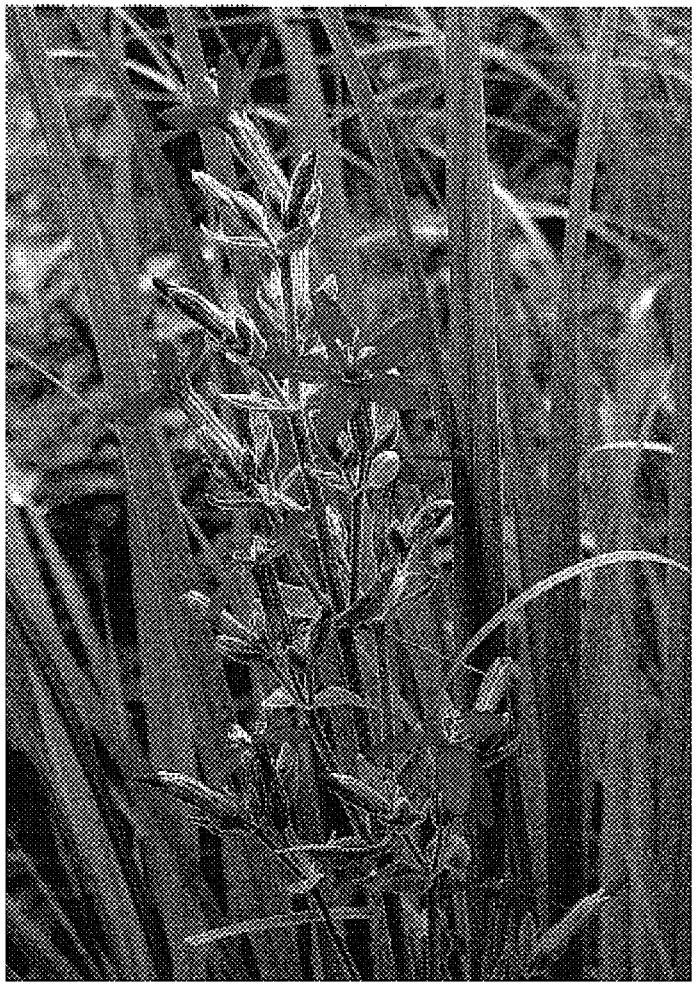

The photograph in FIG. 2 is a close up view of the flowers.

Figure 3:
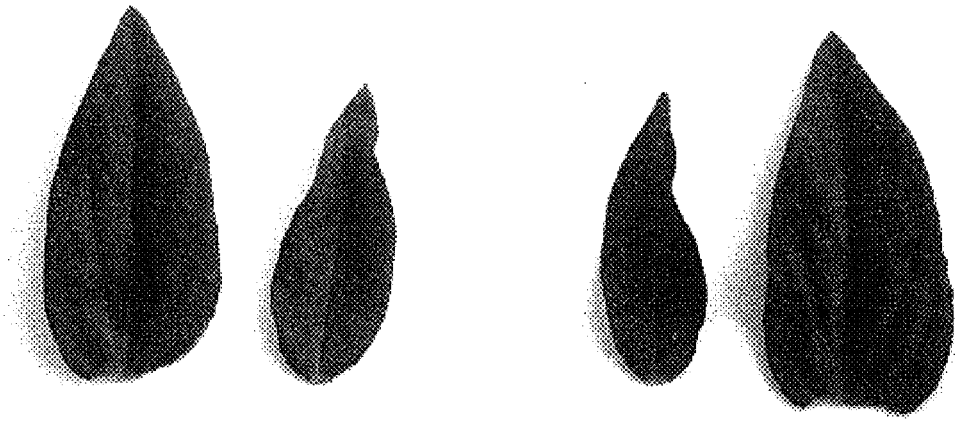

FIG. 3 is a photograph of a comparison between typical leaves of the 'Prairie Fire' (two outer leaves) and typical leaves of the species *Silene regia* (two inner leaves).

The colors in the photographs are as close as possible with the photographic and printing technology utilized. The color values cited in the detailed botanical description accurately describe the colors of the new *Silene.*

DETAILED BOTANICAL DESCRIPTION

The following is a detailed description of the new cultivar as grown outdoors in fertile, well drained garden soil in full sun. The plants were grown for 2 years from a 32-cell liner. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Prairie Fire' is a cultivar of *Silene regia.*
Common name: Prairie Fire Royal Catchfly.
Parentage: Naturally occurring mutant seedling of *Silene regia.*
General description:
*Blooming period.*—About 6 weeks from mid to late summer.

*Plant habit.*—Herbaceous perennial, clump-forming, upright, all shoots arise from base, no secondary branching.

*Growth rate.*—Moderate growth rate, 4 to 5 shoots develop in two growing seasons.

*Height and spread.*—80 to 115 cm (about 3.5 ft) in height, 25 cm (about 10 in) in width.

*Hardiness.*—Zone 4.

*Culture.*—Prefers well-drained to moist soils in full sun to partial shade.

*Diseases and pests.*—No susceptibility or resistance to diseases or pests known to affect *Silene regia* has been observed for 'Prairie Fire'.

*Root description.*—Tap rooted with fleshy secondary roots.

Growth and propagation:

*Propagation.*—Stem cuttings and tissue culture (preferred).

*Root development.*—Transplants from stage 3 tissue culture fully develop a 72 cell plug in 6 to 8 weeks when grown in soil-less media in a greenhouse conditions with bottom heat and an air temperature of 68°. Supplemental light is provided only in winter months; 12:00 AM to 7 AM.

Stem description:

*Shape.*—Round, hollow.

*Stem color.*—144A.

*Stem size.*—Approximately 5 to 8 mm in diameter, up to about 45 cm in length (including peduncle).

*Stem surface.*—Glandular-pubescent (slightly glutinous).

*Internode length.*—3.5 to 5.0 cm in length.

*Branching.*—Basal branches only.

Foliage description:

*Leaf shape.*—Ovate.

*Leaf division.*—Simple.

*Leaf base.*—Cuneate.

*Leaf apex.*—Acute.

*Leaf venation.*—Tri-nerved, center vein on upper surface is a greyed-purple in color (184B) and typically extends two-thirds of the distance from the base.

*Leaf margins.*—Serrate.

*Leaf attachment.*—Petiolate.

*Leaf arrangement.*—Opposite.

*Leaf surface.*—Upper: scabrous. Lower: very fine, short hairs.

*Leaf color.*—Immature: upper; 147A, lower: 147B. Mature: upper; intermediate between 137A and 139A; lower; 138A.

Flower description:

*Type.*—Single, bell-shaped, flaring from the base, arranged on spikes arising from leaf axils, flowers face outward from all sides of the flower stem.

*Fragrance.*—None.

*Lastingness.*—Up to 7 days, self cleaning and not persistent, blooms can be held for 7 to 10 days as a cut flower.

*Quantity.*—Up to about 75 flowers per spike.

*Size.*—2.5 cm in depth, 1.3–1.9 cm in height.

*Peduncle.*—Held at a 30° angle to stem, 1.25–5 cm in length, 3 mm in width, color 138A to 138C.

*Petal description.*—5, ovate in shape, dull in appearance with faint reddish longitudinal veining, acute apex, margins edged with glandular hairs.

*Petal size.*—1.3–1.9 cm in length, 1 cm in width.

*Petal color.*—Upper surface 12A to 14B, lower surface 12A (opening and fully open).

*Calyx description.*—Sepals 5, linear to lanceolate in shape, acute apex, rough, pubescent surface.

*Sepal size.*—3–5 mm in length, 3 mm in width.

*Calyx color.*—Upper and lower surface of sepals; centers 144A, margins 162B.

*Buds.*—Cup-shaped, up to 8 mm in diameter, phyllary are 138B in color, and the tips of the disk flowers are 183B just prior to opening.

*Peduncle.*—Flexible, 7 to 9 cm in length and about 2 mm in diameter, 187A in color, texture is pubescent with very fine hairs.

Reproductive organs:

*Gynoecium.*—Pistil is 4 mm in length and 0.3 mm in width, style is 166C in color, bifid stigma is 166A in color. Ovary is triangular in shape, inferior, single-celled, 4 mm in length and 2 mm in width, 71A in color with the top 1 mm 200A.

*Androcoecium.*—5 stamens, fused, 2 mm in length and 0.25 mm in width, 166A in color, pollen is moderately abundant and 12A in color.

*Fruit.*—An achene, 4 mm in length and 1 mm in width, 200C in color. No seeds were observed in 2003.

It is claimed:

1. A new and distinct cultivar of *Silene* plant named 'Prairie Fire' as herein illustrated and described.

* * * * *